US008168382B2

(12) United States Patent
Lo et al.

(10) Patent No.: US 8,168,382 B2
(45) Date of Patent: May 1, 2012

(54) METHODS FOR DETECTING DNA ORIGINATING FROM DIFFERENT INDIVIDUALS

(75) Inventors: Yuk Ming Dennis Lo, Kowloom (HK); Lit Man Poon, Tsuen Wan (HK)

(73) Assignee: The Chinese University of Hong Kong, Shatin, New Territorries (HK)

(*) Notice: Subject to any disclaimer, the term of this patent is extended or adjusted under 35 U.S.C. 154(b) by 66 days.

(21) Appl. No.: 12/250,480

(22) Filed: Oct. 13, 2008

(65) Prior Publication Data
US 2009/0170102 A1 Jul. 2, 2009

Related U.S. Application Data

(60) Continuation of application No. 11/075,092, filed on Mar. 7, 2005, now abandoned, which is a division of application No. 09/944,951, filed on Aug. 31, 2001, now Pat. No. 6,927,028.

(51) Int. Cl.
*C07H 21/04* (2006.01)
*C12Q 1/68* (2006.01)
(52) U.S. Cl. ...... 435/6.1; 435/6.11; 435/6.12; 435/69.1; 435/69.2
(58) Field of Classification Search .................. None
See application file for complete search history.

(56) References Cited

U.S. PATENT DOCUMENTS

| | | | |
|---|---|---|---|
| 6,017,704 A * | 1/2000 | Herman et al. | 435/6 |
| 6,251,594 B1 | 6/2001 | Gonzalgo et al. | |
| 6,258,540 B1 * | 7/2001 | Lo et al. | 435/6 |
| 6,927,028 B2 | 8/2005 | Dennis et al. | |

FOREIGN PATENT DOCUMENTS

WO WO 98/39474 A1 9/1998

OTHER PUBLICATIONS

Ambinder et al (Cancer Biology, vol. 9, pp. 369-375, 1999).*
Brown et al (Am. J. of Medical Genetics, vol. 64, pp. 191-195, 1996).*
Rousseau et al. (NEJM, vol. 325, No. 1673-1681, 1991).*
LoCoco (Blood, vol. 82, No. 2, Jul. 1993, pp. 606-612).*
Kumar et al. (J. of Biological Chemistry, vol. 263, No. 25, pp. 12645-12652, 1988).*
Turhan et al. (J. Clin. Invet. vol. 81, pp. 1999-2003, Jun. 1988).*
Uehara et al. (J. Hum. Gent. vol. 45, pp. 119-126, 2000).*
Ahern, The Scientist, vol. 9, No. 15, p. 20, 1995.
Avent et al, "Prenatal Determination of Fetal Blood Group Status" *Vox Sang*, 78:155-162 (2000).
Ambinder et al.; Cancer Biology, vol. 9, pp. 369-375, 1999.
Amicucci et al., "Prenatal Diagnosis of Myotonic Dystrophy Using Fetal DNA Obtained from Maternal Plasma" *Clin Chem*, 46(2):301 (2000).
Bianchi, "Fetal DNA in Maternal Plasma: The Plot Thickens and the Placental Barrier Thins" *Am J Hum Genet*, 62:763-764 (1998).
Brown et al.; American Journal of Medical Genetics, vol. 64, pp. 191-195, 1996.
Chen et al., "Fetal DNA in Maternal Plasma: The Prenatal Detection of a Paternally Inherited Fetal Aneuploidy" *Prenat Diagn*, 20(4):355-357 (2000).
Chen et al., "Fetal DNA Analyzed in Plasma from a Mother's Three Consecutive Pregnancies to Detect Paternally Inherited Aneuploidy" *Clin Chem*, 47:937-939 (2001).
Eads et al., "MethyLight: A High-Throughput Assay to Measure DNA Methylation" *Nucleic Acids Res*, 28(8):E32 (2000).
Esteller, et al., "Detection of Aberrant Promoter Hypermethylation of Tumor Suppressor Genes in Serum DNA from Non-Small Cell Lung Cancer Patients" *Cancer Res*, 59(1):67-70 (1999).
Faas et al., "Detection of Fetal RHD-specific Sequences in Maternal Plasma" *Lancet*, 352(9135):1196 (1998).
Graves, "Genomic Imprinting, Development and Disease—is Preeclampsia Caused by a Maternally Imprinted Gene?" *Reprod Fertil Dev*, 10(1):23-29 (1998).
Grunau et al., "Large-scale Methylation Analysis of Human Genomic DNA Reveals Tissue-specific Differences Between the Methylation Profiles of Genes and Pseudogenes" *Hum Mol Genet*, 9(18):2651-2663 (2000).
Herman et al., "Methylation-specific PCR: A Novel PCR Assay for Methylation Status of CpG Islands" *Proc Natl Acad Sci USA*, 93:9821-9826 (1996).
Kawakami et al., "Hypermethylated APC DNA in Plasma and Prognosis of Patients With Esophageal Adenocarcinoma" *J Natl Cancer Inst*, 92(22):1805-1811 (2000).
Kubota et al., "Methylation-specific PCR Simplifies Imprinting Analysis" *Nat Genet*, 16(1):16-17 (1997).
Kuromitsu et al., "A Unique Downregulation of h2-Calponin Gene Expression in Down Syndrome: A Possible Attenuation Mechanism for Fetal Survival by Methylation at the CpG Island in the Trisomic Chromosome 21" *Mol Cell Biol*, 17(2):707-712 (1997).
Lo et al., "Presence of Fetal DNA in Maternal Plasma and Serum" *Lancet*, 350:9076:485-487 (1997).
Lo et al., "Prenatal Diagnosis of Fetal RhD Status by Molecular Analysis of Maternal Plasma" *N Eng J Med*, 339(24):1734-1738 (1998).
Lo et al., "Quantitative Analysis of Fetal DNA in Maternal Plasma and Serum: Implications for Noninvasive Prenatal Diagnosis" *Am J. Hum Genet*, 62:768-775 (1998).
Lo, et al., "Quantitative Analysis of the Bidirectional Fetomaternal Transfer of Nucleated Cells and Plasma DNA" *Clin Chem*, 46(9):1301-1309 (2000).

(Continued)

*Primary Examiner* — Jeanine A Goldberg
(74) *Attorney, Agent, or Firm* — Kilpatrick Townsend & Stockton LLP

(57) ABSTRACT

In a first aspect, the present invention features methods for differentiating DNA species originating from different individuals in a biological sample. These methods may be used to differentiate or detect fetal DNA in a maternal sample or to differentiate DNA of an organ donor from DNA of an organ recipient. In preferred embodiments, the DNA species are differentiated by observing epigenetic differences in the DNA species such as differences in DNA methylation. In a second aspect, the present invention features methods of detecting genetic abnormalities in a fetus by detecting fetal DNA in a biological sample obtained from a mother. In a third aspect, the present invention features methods for differentiating DNA species originating from an organ donor from those of an organ recipient. In a fourth aspect, the present invention features kits for differentiating DNA species originating from different individuals in a biological sample.

32 Claims, 4 Drawing Sheets

OTHER PUBLICATIONS

Lo et al., "Application of a Polymorphic Y Microsatellite to the Detection of Post Bone Marrow Transplantation Chimaerism" *Br J Haematol*, 89(3):645-649 (1995).

Lo et al., "Presence of Donor-specific DNA in Plasma of Kidney and Liver-transplant Recipients" *Lancet*, 351(9112):1329-1330 (1998).

Lo, "Fetal DNA in Maternal Plasma: Biology and Diagnositic Applications" *Clin Chem*, 46(12):1903-1906 (2000).

Lo et al., "Fetal Cells in Maternal Blood: Prospects for Noninvasive Prenatal Diagnosis" *Ann N Y Acad Sci*, 731:204-213 (1994).

Lo et al., "Increased Fetal DNA Concentrations in the Plasma of Pregnant Women Carry Fetuses with Trisomy 21" *Clin Chem*, 45(10):1747-1751 (1999).

Lo et al., "Two-way Cell Traffic Between Mother and Fetus: Biologic and Clinical Implications" *Blood*, 88(11):4390-4395 (1996).

LoCoco; Blood, vol. 82, No. 2, pp. 606-612, 1993.

Maloney et al., "Microchimerism of Maternal Origin Persists into Adult Life" *J Clin Invest*, 104(1):41-47 (1999).

Mangioni et al., "Long-term Persistence of Hemopoietic Chimerism Following Sex-Mismatched Bone Marrow Transplantation" *Bone Marrow Transplant*, 20:969-973 (1997).

Nakagawa et al., "Loss of Imprinting of the Insulin-like Growth Factor II Gene Occurs by Biallelic Methylation in a Core Region of H19-associated CTCF-binding Sites in Colorectal Cancer" *Proc Natl Acad Sci USA*, 98(2):591-596 (2001).

Newton et al., "Analysis of Any Point Mutation in DNA. The Amplification Refractory Mutation System (ARMS)" *Nucleic Acids Res*, 17:2503-2516 (1989).

Nuovo et al., "In Situ Detection of the Hypermethylation—induced Inactivation of the p16 Gene as an Early Event in Oncogenesis" *Proc Natl Acad Sci USA*, 96(22):12754-12759 (1999).

Ohgane et al., "Analysis of CpG Islands of Trophoblast Giant Cells by Restriction Landmark Genomic Scanning" *Dev Genet*, 22(2):132-140 (1998).

Pertl et al., "Detection of Male and Female Fetal DNA in Maternal Plasma by Multiplex Fluorescent Polymerase Chain Reaction Amplification of Short Tandem Repeats" *Hum Genet*, 106:45-49 (2000).

Poon et al., "Prenatal Detection of Fetal Down's Syndrome From Maternal Plasma" *Lancet*, 356:1819-1820 (2000).

Poon, Leo L.M. et al.; "Differential DNA Methylation between Fetus and Mother as a Strategy for Detecting Fetal DNA in Maternal Plasma"; 2002, *Clinical Chemistry*, vol. 48, No. 1, pp. 35-41.

Rousseau et al.; Science, vol. 252, pp. 1097-1102, 1991.

Roux et al., "Evolution of Mixed Chimerism After Allogenic Bone Marrow Transplantation as Determined on Granulocytes and Mononuclear Cells by the Polymerase Chain Reaction" *Blood*, 79:2775-2783 (1992).

Saito et al., "Prenatal DNA Diagnosis of a Single-gene Disorder From Maternal Plasma" *Lancet*, 356:1170 (2000).

Starzl et al., "Chimerism After Organ Transplantation" *Curr Opin Nephrol Hypertens*, 6:292-298 (1997).

Suzuki, Hiromu et al.; "Quantitative DNA methylation analysis by fluorescent polymerase chain reaction single-strand conformation polymorphism using an automated DNA sequencer"; 2000, Electrophoresis, vol. 21, pp. 904-908.

Tang et al., "Detection of Fetal-derived Paternally Inherited X-Chromosome Polymorphisms in Maternal Plasma" *Clin Chem*, 45(11):2033-2035 (1999).

Van Wijk et al., "Detection of Apoptotic Fetal Cells in Plasma of Pregnant Women" *Clin Chem*, 46(5):729-731 (2000).

Wolffe et. al, "Epigenetics: Regulation Through Repression" *Science*, 286:481-486 (1999).

Wolffe, "Transcriptional Control: Imprinting Insulation" *Curr Biol.*, 10:R463-R465 (2000).

Wong et al., "Detection of Aberrant p16 Methylation in the Plasma and Serum of Liver Cancer Patients" *Cancer Res*, 59(1):71-73 (1999).

Yamane, A. et al.; "X chromosome methylation-based chimerism assay for sex-mismatched hematopoietic stem cell transplantation"; 2001, Bone Marrow Transplantation, vol. 28, pp. 969-973.

Yan et al., "CpG Island Arrays: An Application Toward Deciphering Epigenetic Signatures of Breast Cancer" *Clin Cancer Res*, 6:1432-1438 (2000).

Yu et al., "Gene Identification and DNA Sequence Analysis in the GC-poor 20 Megabase Region of Human Chromosome 21" *Proc Natl Acad Sci USA*, 94(13):6862-6867 (1997).

Zhang et al., "Presence of Donor-and Recipient-derived DNA in Cell-free Urine Samples of Renal Transplantation Recipients: Urinary DNA Chimerism" *Clin Chem*, 45(10):1741-1746 (1999).

Zhong et al., "Fetal DNA in Maternal Plasma is Elevated in Pregnancies with Aneuploid Fetuses" *Prenat Diagn*, 20:795-798 (2000).

Lo et al., "Quantitative Analysis of Aberrant p16 Methylation Using Real-Time Quantitative Methylation-specific Polymerase Chain Reaction" *Cancer Res*, 59:3899-3903 (1999).

* cited by examiner

*a* Maternal DNA

T A T G G A

Maternal Plasma

T A T A/G G A

*b*

Primer only

Control (G allele)

Control (A allele)

Maternal DNA (sample 1)

Maternal Plasma (sample 1)

Maternal DNA (sample 2)

Maternal Plasma (sample 2)

25 nt    27 nt    30 nt

*c*

Primer only

Control (G allele)

Control (A allele)

Maternal DNA

Maternal Plasma 25 nt  27 nt    30 nt

SEQUENCE LISTING

<160> NUMBER OF SEQ ID NOS: 11

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:androgen
      receptor gene methylated sequence
      methylation-specific PCR (MSP) primer M-for

<400> SEQUENCE: 1
gcgagcgtag tattttttcgg c                                            21

<210> SEQ ID NO 2

```
<211> LENGTH: 27
<212> TYPE: DNA
<213> ORGANISM: Artificial Sequence
<220> FEATURE:
<223> OTHER INFORMATION: Description of Artificial Sequence:androgen
      receptor gene methylated sequence
      methylation-specific PCR (MSP) primer M-rev

<400> SEQUENCE: 2
aaccaaataa cctataaaac ctctacg                                              27

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:androgen
      receptor gene unmethylated sequence
      methylation-specific PCR (MSP) primer U-for

<400> SEQUENCE: 3
gttgtgagtg tagtattttt tggt                                                 24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:androgen
      receptor gene unmethylated sequence
      methylation-specific PCR (MSP) primer U-rev

<400> SEQUENCE: 4
caaataacct ataaacctc taca                                                  24

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:single
      nucleotide polymorphism (SNP) within
      differentially methylated region (DMR) of human
      IGF2-H19 region amplification PCR forward primer

<400> SEQUENCE: 5
ggacggaatt ggttgtagtt                                                      20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:single
      nucleotide polymorphism (SNP) within
      differentially methylated region (DMR) of human
      IGF2-H19 region amplification PCR reverse primer

<400> SEQUENCE: 6
aggcaattgt cagttcagta a                                                    21

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:single
      nucleotide polymorphism (SNP) site within
      differentially methylated region of human IGF2-H19
      region methylated allele methylation-specific PCR
```

-continued (MSP) forward primer M-for

<400> SEQUENCE: 7
ttaattgggg ttcgttcg                                              18

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:single
      nucleotide polymorphism (SNP) site within
      differentially methylated region of human IGF2-H19
      region methylated allele methylation-specific PCR
      (MSP) reverse primer M-rev

<400> SEQUENCE: 8
cccgacctaa aaatctaata cga                                        23

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:single
      nucleotide polymorphism (SNP) site within
      differentially methylated region of human IGF2-H19
      region unmethylated allele methylation-specific PCR
      (MSP) forward primer U-for

<400> SEQUENCE: 9
ggtttgtttg tggaaatgtt tt                                         22

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:single
      nucleotide polymorphism (SNP) site within
      differentially methylated region of human IGF2-H19
      region unmethylated allele methylation-specific PCR
      (MSP) reverse primer U-rev

<400> SEQUENCE: 10
cccaacctaa aaatctaata caa                                        23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:primer
      extension assay Cys-5-labeled primer

<400> SEQUENCE: 11
gggttatttg ggaataggat attta                                      25

METHODS FOR DETECTING DNA ORIGINATING FROM DIFFERENT INDIVIDUALS

CROSS-REFERENCES TO RELATED APPLICATIONS

This application is a continuation of U.S. application Ser. No. 11/075,092, filed Mar. 7, 2005, now abandoned, which is a division of U.S. application Ser. No. 09/944,951, filed Aug. 31, 2001, now U.S. Pat. No. 6,927,028, the contents of which are herein incorporated by reference in their entirety.

BACKGROUND OF THE INVENTION

The presence of DNA originating from different individuals in bodily fluids is a well-known biological phenomenon in many clinical and biological scenarios. For example, following bone marrow transplantation, the hemopoietic system of the transplantation recipient will consist of varying proportions of donor's and recipient's cells. The ascertainment of the amount of donor's or recipient's cells has been performed by the detection of genetic differences between the donor and recipient, including gender (Mangioni et al, *Bone Marrow Transplant* 20:969-73 (1997)) and DNA polymorphisms (Roux et al., *Blood* 79:2775-83 (1992)). The corollary of this approach is that if the analysed region does not bear a genetic difference between the donor and recipient, then analysis by the current approach will not be possible.

In another example, during pregnancy, detection of fetal DNA in maternal plasma and serum has been previously demonstrated (Lo et al., *Lancet* 350:9076: 485-7 (1997)). This technology has demonstrated that fetal DNA isolated from maternal plasma and serum can be used for non-invasive prenatal diagnosis (Lo et al., *N Eng J Med,* 339(24):1734-8 (1998); Faas et al., *Lancet* 352(9135):1196 (1998); Amicucci et al., *Clin Chem* 46(2):301 (2000); Chen et al., *Prenat Diagn* 24355-7 (2000); Saito et al., *Lancet* 356:1170 (2000)). The clinical application of this phenomenon has been helped by the relatively high absolute and relative concentrations of such circulating fetal DNA in maternal plasma and serum (Lo et al., *Am J. Hum Genet* 62:768-775 (1998)). Using this approach, noninvasive prenatal detection of a number of conditions has been achieved, including fetal rhesus D status (Lo et al., *New Eng J Med* 339:1734-1738 (1998)), myotonic dystrophy (Amicucci et al., *Clin Chem* 46:301-302 (2000)), achondroplasia (Saito et al., *Lancet* 356:1170 (2000)) and certain chromosomal translocations (Chen et al., *Prenat Diag* 20:335-357 (2000); Chen et al, *Clin Chem* 47:937-939 (2001)). All of these current approaches have utilized the detection of DNA sequences inherited from the father and which are genetically distinguishable from those of the mother (Bianchi, *Am J Hum Genet* 62(4): 763 (1998). Specifically, the detection of DNA that the fetus has inherited from the mother in maternal plasma or serum has been thought to be impossible. Similar limitations have also been described for the detection of fetal nucleated cells isolated from the cellular fraction of maternal blood (Lo et al., *Ann N Y Acad Sci,* 731:204 (1994).

Others have detected aberrantly methylated DNA from cancer patients. This has been reported for patients with a variety of cancers, including lung (Esteller, et al., *Cancer Res* 67 (1999)) and liver cancer (Wong et al. *Cancer Res* 71 (1999)).

Recently, much interest has been focused on the biology of epigenetic phenomena, namely processes which alter the phenotype but which are not associated with changes in DNA sequence (Wolffe, *Science* 286:481-486 (1999)). One of the best characterised epigenetic processes is DNA methylation (Wolffe et al., *Curr Biol.* 10:R463-R465 (1999)). A method for discriminating DNA species originating from different individuals in biological fluids using epigenetic, rather than genetic differences between the DNA species would be highly valuable. For example, the epigenetic detection of fetal DNA in a maternal sample would provide a significant advancement enabling additional screening and diagnostic methods.

SUMMARY OF THE INVENTION

In a first aspect, the present invention features methods for differentiating DNA species originating from different individuals in a biological sample. In preferred embodiments the methods of the present invention are used to differentiate or detect fetal DNA in a maternal sample or to differentiate DNA of an organ donor from DNA of an organ recipient.

Those of skill in the art will appreciate that the biological sample obtained from an individual may be taken from any fluid or cell sample, however, in preferred embodiments the bodily fluid is plasma or serum. In preferred embodiments, the DNA species are differentiated by observing epigenetic differences in the DNA species such as differences in DNA methylation. For instance, in situations where one DNA species comes from a male, and one DNA species comes from a female, the epigenetic marker may be the inactivated X chromosome of the female individual. In such embodiments, methylated DNA sequences on the inactivated X chromosome may be used to detect DNA originating from the female individual. In some embodiments, the epigenetic differences may be analyzed inside cells. Further, in some embodiments, the epigenetic differences may be analyzed using in-situ methylation-specific polymerase chain reaction. Additionally, the epigenetic differences may be used to sort or isolate cells from the respective individuals or to purify DNA from the respective individuals. The methods according to the present invention may be performed with or without measuring the concentrations of DNA species, however, in preferred embodiments, the concentrations of DNA species with the respective epigenetic differences are measured. Such measuring of concentrations involves measuring the respective DNA methylation differences in embodiments wherein DNA methylation differences is the epigenetic marker. In especially preferred embodiments, sodium bisulfite is added to the biological sample or to the DNA species directly to detect the DNA methylation differences. However, in other embodiments a methylation-specific polymerase chain reaction, as is well known to those skilled in the art, may be used to detect the DNA methylation differences. In yet other embodiments, DNA sequencing or primer extension may be used to detect the methylation differences.

In a second aspect, the present invention features methods of detecting abnormalities in a fetus by detecting fetal DNA in a biological sample obtained from a mother. The methods according to the present invention provide for detecting fetal DNA in a maternal sample by differentiating the fetal DNA from the maternal DNA based upon epigenetic markers such as differences in DNA methylation. Employing such methods, fetal DNA that is predictive of a genetic anomaly or genetically based disease may be identified thereby providing methods for prenatal diagnosis. These methods are applicable to any and all pregnancy-associated conditions for which methylation changes associated with a disease state is identified. Exemplary diseases that may be diagnosed include, for example, preeclampsia, a chromosomal aneuploidy, including but not limited to trisomy 21, Prader-Willi Syndrome, and Angelman Syndrome.

As with the broader differentiating methods of the first aspect of the invention, the biological sample obtained from the mother is preferably plasma or serum. The differentiation between maternal and fetal DNA may be performed with or without quantifying the concentration of fetal DNA in maternal plasma or serum. In embodiments wherein the fetal DNA is quantified, the measured concentration may be used to predict, monitor or diagnose or prognosticate a pregnancy-associated disorder. In preferred embodiments, the particular fetus-derived epigenetic mark is associated with a fetal disorder, and in some embodiments an epigenetic characteristic in fetal cells in the placenta is used as a fetus-specific marker in maternal plasma or serum.

In a third aspect, the present invention features methods for differentiating DNA species originating from an organ donor from those of an organ recipient. As with the broader differentiating methods of the first aspect of the invention, the biological sample obtained is preferably plasma or serum. The differentiation between DNA from the organ donor and organ recipient or potential organ donor and potential organ recipient may be performed with or without quantifying the concentration of DNA in the biological sample. This embodiment is particularly useful in instances when the transplantation is a bone marrow transplantation. Such measurements may be used to predict the clinical progress of the transplantation recipient especially as regards organ rejection.

In a fourth aspect, the present invention features kits for differentiating DNA species originating from different individuals in a biological sample. Such kits are useful, for instance, for differentiating or detecting the presence of fetal DNA in a maternal biological sample or for differentiating DNA from an organ donor or potential organ donor from that of an organ recipient or potential organ recipient. The kits according to the present invention comprise one or more reagents for ascertaining the methylation status of the maternal DNA such as sodium bisulfite and one or more reagents for detecting the presence of DNA such as a gel. Additionally, such kits may include one or more reagents for amplifying the amount of DNA present in the sample such as one or more reagents for performing polymerase chain reaction amplification. Such reagents are well known to those of skill in the art. Further, such kits may include one or more apparatuses for obtaining a maternal DNA sample. Such apparatuses are well known to those skilled in the art. In particular the kits according to the present invention may be used for diagnosing a disease caused all or in part by a genetic anomaly such as a mutation, substitution or deletion in all or part of a DNA sequence present in a fetus. Exemplary diseases that may be diagnosed include, for example, preeclampsia, a chromosomal aneuploidy, including but not limited to trisomy 21, Prader-Willi Syndrome and Angelman Syndrome.

DESCRIPTION OF THE SPECIFIC EMBODIMENTS

Figure 1:
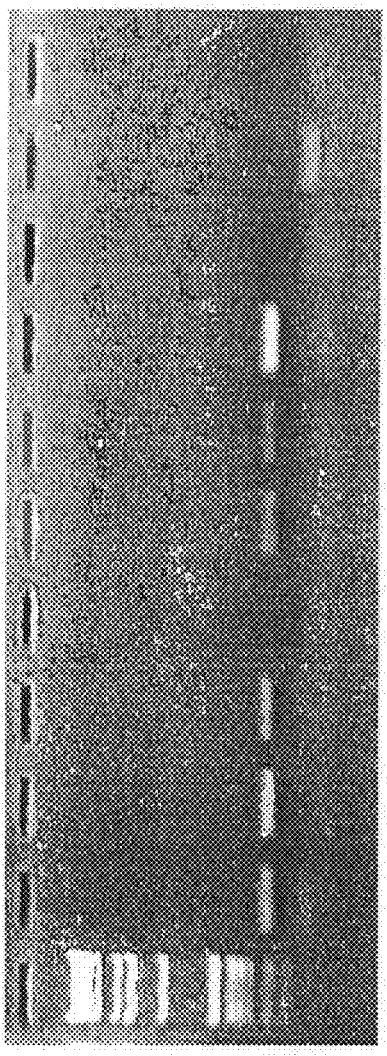
FIG. 1 demonstrates the results of an assay detecting methylated and unmethylated DNA sequences of the androgen receptor gene. In total, 6 male and 11 female healthy subjects were recruited. Of all male control subjects, only the unmethylated androgen receptor gene was detected in these samples as expected (FIG. 1A). By contrast, both unmethylated and methylated androgen receptor gene DNA sequences were observed in female control subjects (FIG. 1A). The detection rates of methylated and unmethylated androgen receptor genes in these female subjects were 100% and 82%, respectively. When DNA samples were omitted from the assay, no positive signal was observed (FIG. 1A). Interestingly, positive signals for both methylated and unmethylated DNA sequences were observed in all male bone marrow transplantation recipients with female donors, indicating cells from female donor exist in the blood circulation of male recipients.
Figure 1:
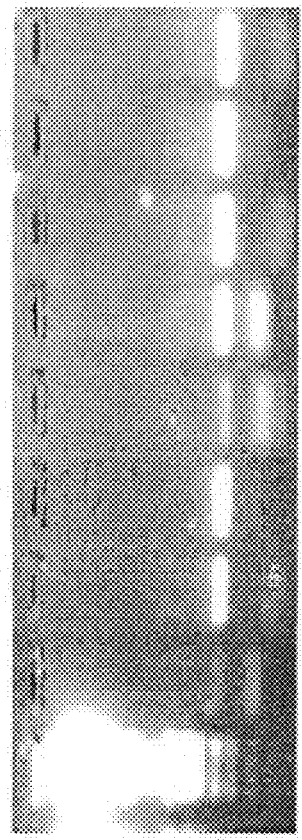

In a first aspect, the present invention features methods for differentiating DNA species originating from different individuals in a biological sample. In preferred embodiments the methods of the present invention are used to differentiate or detect fetal DNA in a maternal sample or to differentiate DNA of an organ donor from DNA of an organ recipient.

Those of skill in the art will appreciate that the biological sample obtained from an individual may be taken from any fluid or cell sample, however, in preferred embodiments the bodily fluid is plasma or serum. In preferred embodiments, the DNA species are differentiated by observing epigenetic differences in the DNA species such as differences in DNA methylation. For instance, in situations where one DNA species comes from a male, and one DNA species comes from a female, the epigenetic marker may be the inactivated X chromosome of the female individual. In such embodiments, methylated DNA sequences on the inactivated X chromosome may be used to detect DNA originating from the female individual. In some embodiments, the epigenetic differences may be analyzed inside cells. Further, in some embodiments, the epigenetic differences may be analyzed using in-situ methylation-specific polymerase chain reaction. Additionally, the epigenetic differences may be used to sort or isolate cells from the respective individuals or to purify DNA from the respective individuals. The methods according to the present invention may be performed with or without measuring the concentrations of DNA species, however, in preferred embodiments, the concentrations of DNA species with the respective epigenetic differences are measured. Such measuring of concentrations involves measuring the respective DNA methylation differences in embodiments wherein DNA methylation differences is the epigenetic marker. In especially preferred embodiments, sodium bisulfite is added to the biological sample or to the DNA species directly to detect the DNA methylation differences. However, in other embodiments a methylation-specific polymerase chain reaction, as is well known to those skilled in the art, may be used to detect the DNA methylation differences. In yet other embodiments, DNA sequencing or primer extension may be used to detect the methylation differences.

As used herein, the term "biological sample" is intended to encompass any fluid or cellular sample or mixture thereof obtained from a living organism. Specifically, the term includes tissue biopsy, serum, plasma or amniotic fluid samples.

As used herein, the term "epigenetic difference" is intended to encompass any molecular or structural difference other than the primary nucleotide sequence. For instance, this may include differences in methylation.

As used herein, the term "DNA" is intended to encompass any sequence of more than one nucleotide such as polynucleotides, gene fragments and complete gene sequences.

As used herein, the term "methylation-specific PCR" is used to describe a method in which DNA is treated with sodium bisulfite and then subjected to PCR amplification. This technique is based on the principle that treating DNA with bisulfite results in conversion of unmethylated cytosine residues into uracil. Methylated cytosine residues, on the other hand, remain unchanged. Thus, the DNA sequences of methylated and unmethylated genomic regions following bisulfite conversion are different and distinguishable by sequence-specific PCR primers.

The present invention utilizes the phenomenon of genomic imprinting to overcome the limitations of the prior art. In genomic imprinting, DNA sequences are modified biochemically, without alteration in DNA sequence. If this process results in differential modification of the fetal and maternal DNA, then this difference can be exploited for the discrimination of fetal from maternal DNA in maternal plasma and serum. This phenomenon can also be used for the discrimination of fetal cells from maternal cells in the cellular fraction of maternal blood. In addition, this principle can also be used to detect maternal cells or DNA that has entered into the body of the fetus/baby (Lo, et al., *Blood* 88(11):4390-5 (1996); Lo, et al, *Clin Chem*, 46(9):1301-9 (2000); Maloney et al., *J Clin Invest* 104(1):41-7 (1999). This phenomenon can also be used in many other clinical scenarios wherein cells or DNA sequences are found to be present inside the body of an individual, such as following bone marrow transplantation (Lo et al., *Br J Haematol* 89(3):645-9 (1995)) or solid organ transplantation (Starzl et al., *Curr Opin Nephrol Hypertens* 6(3):292-8 (1997); Lo et al., *Lancet* 351(9112):1329-30 (1998); Zhang, *Clin Chem* 45(10):1741-6 (1999)).

The present invention allows development of a gender-independent and polymorphism-independent marker for fetal DNA in maternal plasma/serum. To develop a gender-independent and polymorphism-independent fetal marker, one can use DNA sequences which are preferentially and specifically methylated in the trophoblasts (Ohgane et al., *Dev Genet*, 22(2): 132-40 (1998)). This overcomes the current limitation which can only easily detect the presence of DNA from a male fetus in the plasma/serum of the mother (by using the Y-chromosome as the target) (Lo, et al., *Am J Hum Genet*, 62(4):768 (1998). It provides detection methods separate from relying on sequence differences in fetal and maternal DNA to make such a distinction (Tang et al, *Clin Chem* 45(11):2033-5 (1999); Pertl et al., *Hum Genet* 106:45-49 (2000)).

The development of molecular detection methods such as the PCR has provided many powerful tools for the monitoring of chimerism following bone marrow transplantation (BMT). One of the most widely used PCR-based tests for the detection of post-BMT chimerism in sex-mismatched cases is PCR for sequences on the Y chromosome (Lo et al., *Br J Haematol* 89: 645-9 (1995). The limitation of this strategy is that it can only be used in cases wherein the donor is male and the recipient is female. The present invention provides a system that can be applied to situations when the donor is female and the recipient is male. The fact that the phenomenon of Lyonization only exists in females, can be exploited to develop a female-specific marker. In this phenomenon, one of the two X chromosomes in a female individual is inactivated at random, with methylation occurring in a number of the inactivated genes. This therefore allows an assay for detecting female DNA in an excess of male DNA and which can be applied to BMT with female donors and male recipients.

In a second aspect, the present invention features methods of detecting abnormalities in a fetus by detecting fetal DNA in a biological sample obtained from a mother. The methods according to the present invention provide for detecting fetal DNA in a maternal sample by differentiating the fetal DNA from the maternal DNA based upon epigenetic markers such as differences in DNA methylation. Employing such methods, fetal DNA that is predictive of an anomaly or a disease may be identified thereby providing methods for prenatal diagnosis. These methods are applicable to any and all pregnancy-associated conditions for which methylation changes associated with a disease state is identified. Exemplary diseases that may be diagnosed include, for example, preeclampsia, a chromosomal aneuploidy, including but not limited to trisomy 21, Prader-Willi Syndrome, and Angelman Syndrome.

As with the broader differentiating methods of the first aspect of the invention, the biological sample obtained from the mother is preferably plasma or serum. The differentiation between maternal and fetal DNA may be performed with or without quantifying the concentration of fetal DNA in maternal plasma or serum. In embodiments, wherein the fetal DNA is quantified, the measured concentration may be used to predict, monitor or diagnose a pregnancy-associated disorder. In preferred embodiments, the particular fetus-derived epigenetic mark is associated with a fetal disorder, and in some embodiments an epigenetic characterisitic in fetal cells in the placenta is used as a fetus-specific marker in maternal plasma or serum.

The present invention utilizes differentially methylated fetal DNA sequences, which do not need to be distinguishable in terms of DNA sequence from maternal DNA, as markers for non-invasive prenatal diagnosis. This novel approach can convert fetus-mother pairs who are not informative in the conventional approach, to being informative for prenatal diagnosis. Thus, present invention provides a platform on which a new generation of non-invasive prenatal tests can be built.

The methods of the present invention are based on the detection of differently methylated DNA of fetal origin in the plasma or serum of pregnant women. Differentially methylated DNA sequences, which may contain single nucleotide polymorphism, are preferably detected by methylation-specific polymerase chain reaction (PCR); but in principle any detection method for differentially methylated DNA can be used. This approach allows the use of conventional uninformative fetal DNA markers for prenatal diagnosis.

The present invention allows detecting or predicting the presence of any disorders of the fetus or the mother which are associated with a change in methylation status of a DNA sequence. Examples include imprinting disorders such as Prader-Willi syndrome (Kubota et al., *Nat Genet* 16(1):16-7 (1997). The present invention provides a new type of test for preeclampsia which has been suggested to be an imprinting disorder (Graves, *Reprod Fertil Dev* 10(1):23-9 (1998). The present invention further provides a new type of test for chromosomal aneuploidies, including Down syndrome (trisomy 21), which may be associated with methylation changes (Yu et al., *Proc Natl Acad Sci USA* 94(13):6862-7 (1997).

The present invention features using DNA methylation differences between the mother and fetus thereby overcoming the limitations of the prior art in the detection of fetal DNA in maternal plasma.

In a third aspect, the present invention features methods for differentiating DNA species originating from an organ donor from those of an organ recipient. As with the broader differentiating methods of the first aspect of the invention, the biological sample obtained is preferably plasma or serum. The differentiation between DNA from the organ donor and organ recipient or potential organ donor and potential organ recipient may be performed with or without quantifying the concentration of DNA in the biological sample. This embodiment is particularly useful in instances when the transplantation is a bone marrow transplantation. Such measurements may be used to predict the clinical progress of the transplantation recipient especially as applied to organ rejection.

In a fourth aspect, the present invention features kits for differentiating DNA species originating from different individuals in a biological sample. Such kits are useful, for instance, for differentiating or detecting the presence of fetal DNA in a maternal biological sample or for differentiating DNA from an organ donor or potential organ donor from that of an organ recipient or potential organ recipient. The kits according to the present invention comprise one or more reagents for ascertaining the methylation status of the maternal DNA such as sodium bisulfite and one or more reagents for detecting the presence of DNA such as a gel. Additionally, such kits may include one or more reagents for amplifying the amount of DNA present in the sample such as one or more reagents for performing polymerase chain reaction amplification. Such reagents are well known to those of skill in the art. Further, such kits may include one or more apparatuses for obtaining a maternal DNA sample. Such apparatuses are well known to those skilled in the art. In particular the kits according to the present invention may be used for diagnosing a disease caused all or in part by a genetic anomaly such as a mutation, substitution or deletion or duplication in all or part of a DNA sequence present in a fetus. Exemplary diseases that may be diagnosed include, for example, preeclampsia, a chromosomal aneuploidy, including but not limited to trisomy 21, Prader-Willi Syndrome and Angelman Syndrome.

EXAMPLE 1

Detection of Post-Bone Marrow Transplantation Chimerism using a Novel Epigenetic Approach Materials and Methods Subjects and Samples Four male marrow transplantation recipients, who received bone marrow from female donors, and 17 normal healthy subjects were recruited in this study. Buffy coat (BC) from all recruited EDTA-blood samples were harvested and stored at −20° C. as described (Lo et al., *Am J Hum Genet* 62:768-75 (1998).

DNA Isolation

DNA was extracted from the BC using a Nucleon DNA Extraction Kit (Scotlabs) according to manufacturer's recommendations.

Bisulfite Conversion

Bisulfite modification of DNA samples was performed using a CpGenome DNA Modification Kit (Intergen) as instructed by the manufacturer. With bisulfite conversion, unmethylated cytosine residues are converted to uracil while methylated cytosine residues remain unchanged (Herman et al, *Proc Natl Acad Sci USA* 93:9821-6 (1996). The sequence difference between methylated and unmethylated DNA following bisulfite conversion is then distinguished using different PCR primers. 1 µg of BC DNA was used in a bisulfite conversion reaction.

Methylation-Specific PCR (MSP)

MSP assays were modified from the protocol as described by Herman et al, supra. The primers M-for (5'-GCGAGCG-TAGTATTTTTCGGC-3'; SEQ ID NO: 1) and M-rev (5'-AACCAAATAACCTATAAAACCTCTACG-3'; SEQ ID NO:2) were designed for the methylated sequence, while the primers U-for (5'-GTTGTGAGTGTAGTATTTTTTGGT-3'; SEQ ID NO:3) and U-rev (5'-CAAATAACCTATAAAAC-CTCTACA-3'; SEQ ID NO:4) were designed for the unmethylated sequence. Five µl bisulfite-treated DNA was added to a 50 µl PCR reaction containing 5 µl 10× TaqMan buffer A (PE Applied Biosystems), 2 mM $MgCl_2$, 10 pmol dNTPs, 20 pmol each of the corresponding MSP primers and 1.25 U AmpliTaq Gold DNA polymerase (PE Applied Biosystems). Reaction mixtures were thermal cycled (methylated allele: 95° C. for 45 sec, 58° C. for 30 sec, 72° C. for 20 sec; unmethylated allele: 95° C. for 45 sec, 50° C. for 30 sec, 72° C. for 20 sec) for 45 cycles, with an initial denaturing step of 8 min at 95° C. PCR products were then analyzed by agarose gel electrophoresis.

Results

This experiment provides a MSP assay to detect methylated and unmethylated DNA sequences of the androgen receptor gene. In total, 6 male and 11 female health subjects were recruited. Of all male control subjects, only the unmethylated androgen receptor gene was detected in these samples as expected (FIG. 1A). By contrast, both unmethylated and methylated androgen receptor gene DNA sequences were observed in female control subjects (FIG. 1A). The detection rates of methylated and unmethylated androgen receptor genes in these female subjects were 100% and 82%, respectively. When DNA samples were omitted from MSP assay, no positive signal was observed (FIG. 1A). Interestingly, positive signals for both methylated and unmethylated DNA sequences were observed in all male sex-mismatched bone marrow transplantation recipients (100%), indicating cells from female donor exist in the blood circulation of male recipients.

These results demonstrate, for the first time that methylated genes on the inactivated X chromosome from female individuals can be used as a female-specific marker in chimerism research. This assay is also applicable to the study of other types of post-transplantation chimerisms involving mixture of male and female cells or DNA. Examples include cellular chimerism following solid organ transplantation (Starzl et al., *Curr Opin Nephrol Hypertens* 6:292-8 (1997)), post-transplantation plasma DNA chimerism (Lo et al., *Lancet* 351: 1329-30 (1998)) and urinary DNA chimerism (Zhang et al., *Clin Chem* 45: 1741-6 (1995)). In addition, there is also much recent interest in the passage of cells and DNA from the mother into the fetus during pregnancy (Lo et al., *Blood* 88:4390-5. (1996); Maloney et al., *J Clin Invest* 104: 41-7 (1999); Lo et al., *Clin Chem* 46:1301-9 (2000). The epigenetic markers developed should also be of used in chimerism of maternal origin in male offsprings.

The current assay may be developed into a quantitative format, using for example, real-time PCR technology (Lo et al, *Cancer Res* 59:3899-903 (1999)). Such development would allow us to monitor the levels of chimerism in a particular person. Clinically such an assay might have a role in the monitoring of graft acceptance in BMT. In the case of urinary or plasma DNA chimerism, such an assay might also be used for the monitoring of graft rejection.

EXAMPLE 2

Differential DNA Methylation Between Fetus and Mother as a Strategy for Detecting Fetal DNA in Maternal Plasma The present experiment demonstrates that by using a differentially methylated region in the human IGF2-H19 locus as an epigenetic marker in maternal plasma, detection of an allele that the fetus has inherited from the mother is possible. These results greatly expand the prenatal diagnostic possibilities of fetal DNA in maternal plasma allowing development of a gender- and polymorphism-independent fetal-specific marker in maternal plasma and new strategies for the prenatal diagnosis of imprinting disorders and certain chromosomal aneuploidies.

Materials and Methods

Subjects and Samples

Samples were collected from pregnant women with informed consent. In total, 21 and 18 women in the second trimester (17-21 weeks) and third trimester (37-42 weeks) of pregnancy, respectively, were recruited for this study. None of the recruited subjects had preeclampsia or preterm labor in the current pregnancy. EDTA maternal blood and fetal amniotic fluid samples were collected from the second trimester cases as described previously (Lo et al., *Am J Hum Genet* 62:768-775 (1998)). For the third trimester cases, we collected EDTA maternal blood samples at 2 to 3 h before normal vaginal delivery. EDTA fetal cord blood samples were also collected immediately after delivery as described (Lo et al., *Clin Chem* 46:1903-1906 (2000)). Plasma and buffy coat from all recruited blood samples were harvested and stored at −20° C. as described (Lo et al., *Am J Hum Genet* 62:768-775 (1998)), except that plasma samples were recentrifuged at 16,000 g. Amniotic fluid samples were stored at 4° C.

DNA Isolation

DNA was extracted from plasma and amniotic fluid samples using a QIAamp Blood Kit (Qiagen). Typically, 800 µl of plasma or amniotic fluid was used for DNA extraction per column. An elution volume of 50-110 µL was used. DNA was extracted from the buffy coat using a Nucleon DNA Extraction Kit (Scotlabs) according to manufacturer's recommendations.

Genotyping of the DMR Polymorphic Region

Figure 2:
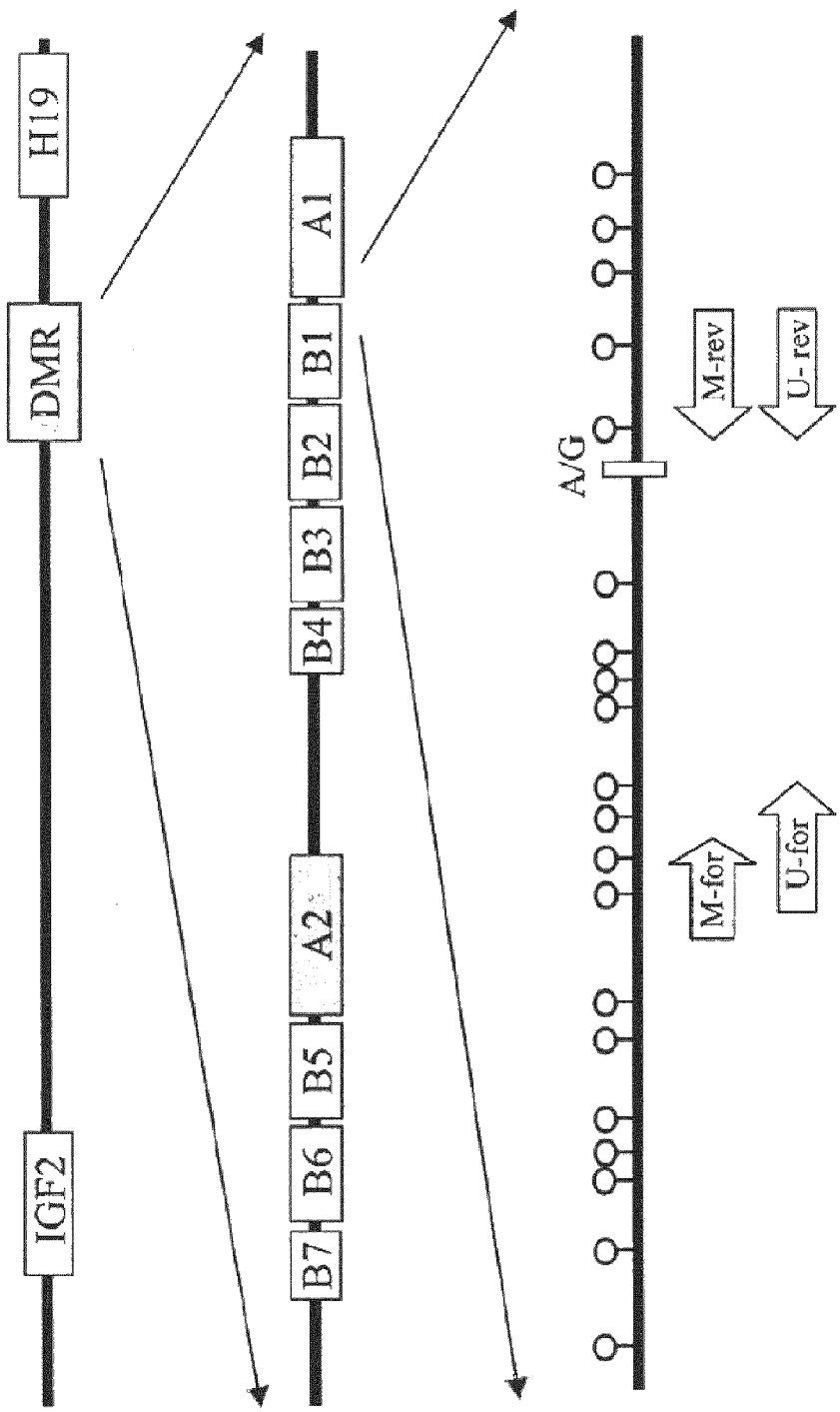
FIG. 2 provides a schematic representation of the differentially methylated region (DMR) of the human IGF2-H19 region. The two 450-bp repeat (A1 and A2) and seven 400-bp repeat (B1-B7) units are shown. The potential methylation sites on the upper strand DNA of the studied region are represented by open circles. The studied single nucleotide polymorphism (SNP) site (A/G) is indicated by an open box. Open arrows represent the location of the forward (for) and reverse (rev) primers in PCR reactions specific for the methylated (M) and unmethylated (U) alleles, respectively. Sequences of these MSP primers are shown (SEQ ID NOS: 7-10). Sequence differences between bisulfite-treated DNA and untreated DNA are highlighted in bold italics and sequence differences between methylated (paternally-inherited) and unmethylated (maternally-inherited) DNA are underlined in bold.

The DMR in the human IGF2-H19 locus contains two 450-bp repeat and seven 400-bp repeat units (Nakagawa et al., *Proc Natl Acad Sci USA* 98:591-596 (2001)) (FIG. 2). An A/G SNP within the DMR (Nakagawa et al, supra) was selected as a marker in our investigation (FIG. 2). Polymerase chain reaction (PCR) was used to amplify the SNP in both maternal and fetal DNA samples. Primers were designed using the sequence of the *Homo sapiens* H19 gene (Genbank accession number AF125183). Typically, 2 to 5 µl eluted DNA, purified from maternal buffy coat, cord buffy coat or amniotic fluid was added to a 25 µl PCR reaction containing 2.5 µl 10× TaqMan buffer A (PE Applied Biosystems), 3 mM MgCl$_2$, 6.26 pmol dNTPs, 5 pmol primers (forward: 5'-ggACG-GAATTGGTTGTAGTT-3' (SEQ ID NO:5); reverse: 5'-AG-GCAATTGTCAGTTCAGTAA-3' (SEQ ID NO:6)) and 0.625 U AmpliTaq Gold DNA polymerase (PE Applied Biosystems) (95° C. for 8 min followed by 35 cycles of 95° C. for 1 min, 56° C. for 20 sec, 72° C. for 20 sec). For the forward primer, the nucleotides in upper case corresponded to positions 7927 to 7944 of the H19 sequence (Genbank accession number AF125183). For the reverse primer, the nucleotides were complementary to positions 8309 to 8329 of the H19 sequence. PCR products were then analysed by agarose gel electrophoresis and DNA sequencing.

Bisulfite Conversion

Bisulfite modification of DNA samples was performed using a CpGenome DNA Modification Kit (Intergen) as instructed by the manufacturer. With bisulfite conversion, unmethylated cytosine residues would be converted to uracil; while methylated cytosine residues would remain unchanged (Herman et al., *Proc Natl Acad Sci USA* 93:9821-9826 (1996)). The sequence difference between methylated and unmethylated DNA following bisulfite conversion could then be distinguished using different PCR primers. In general, 1 µg of buffy coat DNA from maternal or cord blood, or 93 µl eluted DNA purified from maternal plasma or amniotic fluid was used in a bisulfite conversion reaction. Bisulfite-treated DNA was then eluted in 25-50 µl 1µ Tris-EDTA.

Methylation-Specific PCR (MSP)

MSP assays were modified from the protocol as described (Herman et al. 1996). Five µl bisulfite-treated DNA was added to a 50 µl PCR reaction containing 5 µl 10× TaqMan buffer A (PE Applied Biosystems), 2.5 mM MgCl$_2$, 10 pmol dNTPs, 20 pmol each of the corresponding MSP primers (FIG. 2) and 1.25 U AmpliTaq Gold DNA polymerase (PE Applied Biosystems). The primers M-for and M-rev (FIG. 2; SEQ ID NOS:7 and 8) were designed for the methylated sequence, while the primers U-for and U-rev (FIG. 2; SEQ ID NOS:9 and 10) were designed for the unmethylated sequence. Reaction mixtures were thermal cycled (methylated allele: 95° C. for 45 sec, 55° C. for 20 sec, 72° C. for 20 sec; unmethylated allele: 95° C. for 45 sec, 49° C. for 20 sec, 72° C. for 20 sec) for 50 (buffy coat and amniotic fluid DNA) or 56 (plasma DNA) cycles, with an initial denaturing step of 8 min at 95° C. PCR products were then analyzed by agarose gel electrophoresis. Reaction products were purified using Microspin S-300 HR columns (Amersham Pharmacia) for DNA sequencing or the primer extension assay.

DNA Sequencing

Purified PCR products were sequenced using an ABI Prism dRhodamine Terminator Cycle Sequencing Ready Reaction Kit (PE Applied Biosystems) and the corresponding forward primers of the PCR products. Sequencing products were analysed using an ABI Prism 310 Genetic Analyser (PE Applied Biosystems).

Primer Extension Assay

Two µl of the purified MSP product was added to a 25 µl reaction containing 50 µM ddATP (2',3'-dideoxyadenine triphosphate), 50 µM dGTP, 50 µM dTTP, 0.2 pmol Cys-5-labeled primer (5'-GGGTTATTTGGGAATAGGATATTTA-3'; SEQ ID NO:11), 4 U Thermo Sequenase (Amersham Pharmacia) and 1.43 µl concentrated buffer. Reactions were thermal cycled for 40 cycles (95° C. for 30 sec, 51° C. for 20 sec, 72° C. for 20 sec). The Cys-5-labeled primer was 25 nucleotides (nt) in length and the polymorphic site was 2 nt away from the 3'-end of the primer. For the A allele, the incorporation of the ddATP at this polymorphic site would produce chain termination, thus resulting in an extension product of 27 nt (i.e., 25+2 nt). For the G allele, chain extension would continue until the next A residue which was 5 nt away from the 3'-end of the primer, thus resulting in an extension product of 30 nt (i.e., 25+5 nt). Reaction products were electrophoresed using a 14% denaturing polyacrylamide gel and analysed using an ALF Express Sequencer (Amersham Pharmacia). Data were analysed by the AlleleLinks program (Amersham Pharmacia).

Results

Genotyping of DMR

Thirty-nine pregnant women were recruited in this study. Maternal genotype at the SNP within the DMR (FIG. 2) was determined by direct sequencing of PCR products from the buffy coat DNA. The number of pregnant women with each of the possible genotypes were 17 (GG, 43.6%), 16 (AG, 41.0%) and 6 (AA, 15.4%).

Detection of Fetal DNA in Plasma from Women Heterozygous for a Biallelic Polymorphism The 16 women who were heterozygous (i.e., AG) for the SNP were selected for further examination. As this is a biallelic polymorphism, these women would not be considered informative at this polymorphic locus for the detection of fetal DNA in maternal plasma, based on previous criteria (Lo et al., Ann N Y Acad Sci 731:204-213 (1994); Bianchi Am J Hum Genet 62:763-764 (1998)). To demonstrate that differential methylation at this genomic region would allow us to overcome this limitation, maternal DNA was bisulfite-treated and amplified by MSP using the primers shown in FIG. 2. Similarly, fetal DNA isolated from amniotic fluid (2nd trimester samples) or buffy coat of cord blood (3rd trimester samples) was subjected to PCR and MSP to determine the imprinting status of the fetal alleles.

Amongst the 16 selected cases, the methylated (i.e., paternally-inherited) alleles from four 3rd trimester and seven 2nd trimester fetal samples were different from the methylated alleles of the respective mothers (FIGS. 3a,b; compare panels 1 and 2). To test if this differential methylation between fetus and mother would allow the fetal allele to be detected from maternal plasma, maternal plasma DNA from these cases was subjected to bisulfite conversion, followed by MSP. Interestingly, the paternally-inherited methylated fetal allele could be detected in two 3rd trimester and four 2nd trimester maternal plasma samples (FIGS. 3a,b; panels 3). To exclude the possibility that these observations were simply due to the existence of aberrantly methylated maternal DNA in maternal plasma, we collected a postnatal maternal plasma sample (~3.5 years after delivery) from one of the positive cases for further examination. We did not observe the additional methylated allele in this postnatal sample (FIG. 3a, panel 4), indicating that the additional methylated allele in maternal sample during pregnancy was of fetal origin. In addition, no positive signal was observed in the plasma of non-informative cases (n=4, data not shown), thus further demonstrating the specificity of this MSP assay. Taken together, these data indicate that the use of differential methylation between mother and fetus allows detecting fetal DNA in maternal plasma, even in cases which are not considered informative with existing criteria.

Detection of Fetal-Derived Maternally-Inherited DNA from Maternal Plasma

Figure 4:
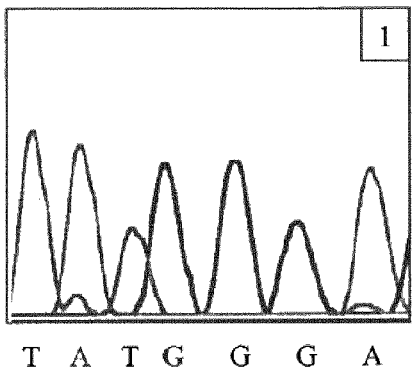
FIG. 4 demonstrates detection of unmethylated (maternally-inherited) fetal DNA in maternal plasma. (a) Unmethylated DNA sequences were detected in maternal buffy coat (panel 1) and a third trimester maternal sample (panel 2) using direct sequencing. The presence of unmethylated fetal DNA in maternal plasma is indicated by *. (b) Unmethylated fetal DNA (arrow) was detected in two third trimester maternal plasma samples using the primer extension assay. (c) Unmethylated fetal DNA (arrow) was detected in a second trimester maternal plasma sample using the primer extension assay. Products from control reactions containing primer only, unmethylated G allele or unmethylated A allele are shown. The sizes (nt) of the reaction products are shown at the bottom. ●, unused primer; □ detected allele.
Figure 4:
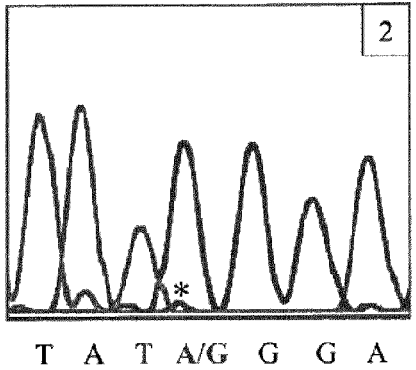
Figure 4:
Figure 4:
Figure 4:
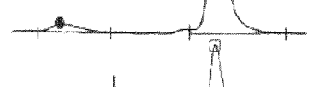
Figure 4:
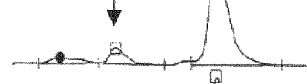
Figure 4:
Figure 4:
Figure 4:
Figure 4:
Figure 4:
Figure 4:
Figure 4:
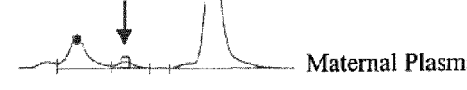

We then tested if the use of differential methylation between mother and fetus might allow us to detect an allele that the fetus has inherited from the mother. This type of analysis has previously been thought to be impossible (Lo et al., Ann N Y Acad Sci 731:204-213 (1994); Bianchi, Am J Hum Genet 62:763-764 (1998)). As the maternally-inherited allele was unmethylated, the primers U-for and U-rev (FIG. 2) were used to amplify the unmethylated allele following bisulfite conversion. Among the 16 analyzed cases, three 3rd trimester and five 2nd trimester maternal samples were informative. In these cases, the fetus possessed an unmethylated allele that was different from the unmethylated allele of the mother. These results implied that in these cases, the mother had originally inherited the fetal allele from her father and then passed on to the fetus. Of these 8 informative cases, only a weak positive signal was observed in one of the 3rd trimester samples on direct sequencing (FIG. 4a, compared panel 1 and panel 2).

We reasoned that the weak signal in this single positive case and the low detection rate of the unmethylated fetal allele from maternal plasma might be due to the low sensitivity of the direct sequencing method. To enhance the sensitivity of detection, we employed a more sensitive primer extension assay to detect the unmethylated fetal allele from the MSP reaction products. As the SNP was an A/G polymorphism, ddATP was used as a reaction substrate in the primer extension assay. Extended reaction products from the A and G alleles were 27 and 30 nt long, respectively. No fetal specific reaction product was present in the corresponding maternal buffy coat samples (FIGS. 4b, c; maternal BC). Strikingly, fetal specific extension products were observed in two 3rd trimester (FIG. 4b, arrow) and one 2nd trimester (FIG. 4c, arrow) maternal plasma samples, indicating the presence of unmethylated fetal DNA in maternal plasma. As controls, none of the tested non-informative cases was positive in this assay (n=5, data not shown). These results demonstrated, for the first time, the feasibility of using epigenetic markers to detect a fetal-derived maternally-inherited DNA sequence from maternal plasma.

Discussion

These results demonstrate that the use of epigenetic markers overcomes the conventional limitations of detecting fetal DNA in maternal plasma. It is possible to detect a paternally-inherited fetal allele, which is genetically indistinguishable from a maternal allele, from the mother's plasma, by the use of epigenetic differences between the mother and fetus. Likewise, it is possible to detect a maternally-inherited fetal allele from maternal plasma. This novel epigenetic approach will therefore expand the repertoire of disorders wherein fetal DNA in maternal plasma can be used.

Figure 3:
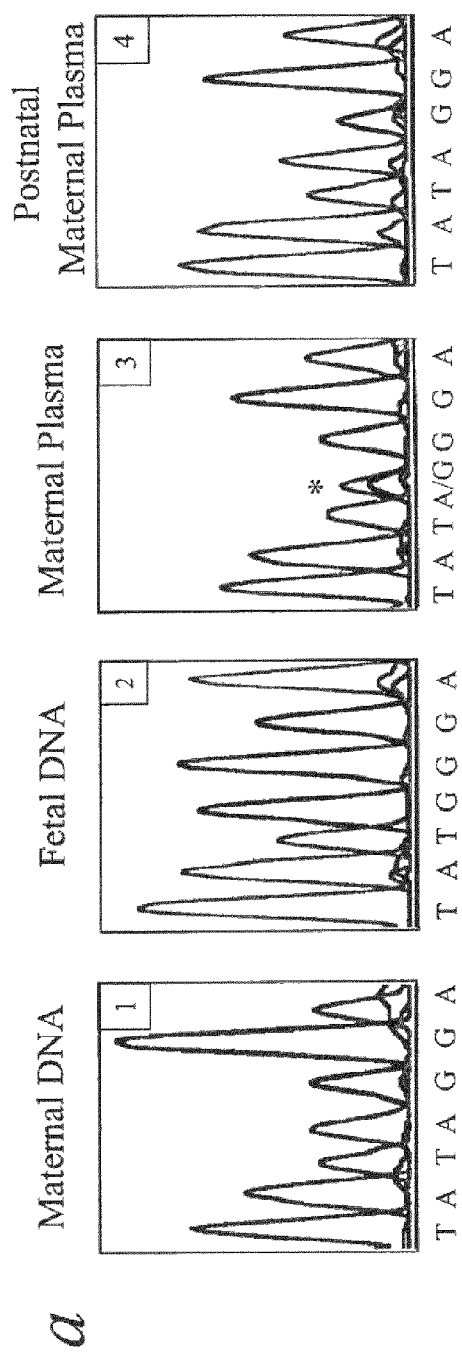
FIG. 3 demonstrates detection of methylated (paternally-inherited) fetal DNA in $3^{rd}$ trimester (a) and $2^{nd}$ trimester (b) maternal plasma. DNA sequence of methylated alleles in maternal buffy coat (panel 1), fetal buffy coat or amniotic fluid (panel 2), prenatal maternal plasma (panel 3) and postnatal maternal plasma (panel 4) samples are shown. The presence of methylated fetal DNA in the prenatal maternal plasma sample is indicated by * The polymorphic (SNP) site is shown in red letters.
Figure 3:
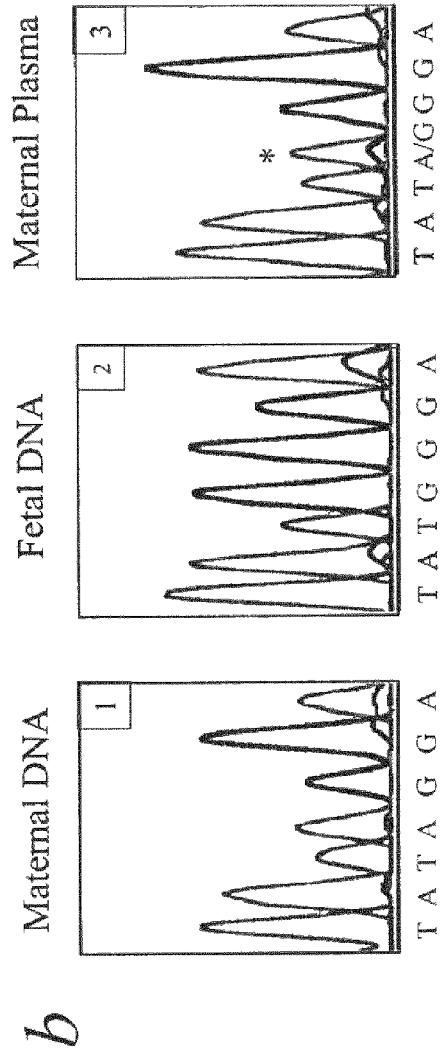

Even with the use of relatively insensitive methods such as direct sequencing and primer extension, the present results demonstrate that it is possible to detect differentially methylated fetal DNA sequences from maternal plasma. There was a lower sensitivity in the detection of the unmethylated fetal DNA in maternal plasma (FIG. 4), as compared with the analogous assay for the methylated allele (FIG. 3). Using more sensitive detection systems, such as allele-specific PCR (Newton et al., *Nucleic Acids Res* 17:2503-2516 (1989)) and real-time methylation-specific PCR (Lo et al., *Cancer Res* 59:3899-3903 (1999); Eads et al., *Nucleic Acids Res* 28:E32 (2000)), might enhance the sensitivity of plasma-based epigenetic analysis. The development of real-time methylation-specific PCR is particularly interesting as it opens up the possibility of quantifying fetal-specific methylation in maternal plasma, as has already been achieved for the detection of tumor DNA in circulation (Kawakami et al., *J Natl Cancer Inst* 92:1805-1811 (2000)).

The possible introduction of fetal DNA in maternal plasma as a routine prenatal diagnostic tool has raised questions with regard to the need of a generic marker for circulating fetal DNA (Lo et al., *Am J Hum Genet* 62:768-775 (1998); Avent et al, *Vox Sang* 78:155-162 (2000)). Most proposals for such a marker have thus far focused on the use of genetic polymorphisms between the mother and fetus (Tang et al., *Clin Chem* 45:2033-2035 (1999); Pertl et al., *Hum Genet* 106:45-49 (2000)). The present demonstration of the feasibility of epigenetic markers for fetal DNA detection in maternal plasma opens up a new approach for the development of a gender-independent and polymorphism-independent fetal marker in maternal plasma. One way wherein this can be achieved is to exploit the phenomenon of tissue-specific methylation (Grunau et al., *Hum Mol Genet* 9:2651-2663 (2000)). As the trophoblast has been suggested to be the predominant cell population for releasing fetal DNA into maternal plasma, the elucidation of trophoblast-specific methylation patterns allows the development of a generic epigenetic fetal marker in maternal plasma. Biologically, the use of tissue-specific methylation markers may also allow one to directly address the question as to what fetal cell types are responsible for releasing fetal DNA into maternal plasma.

The epigenetic analysis of maternal plasma has obvious applications to disorders associated with genomic imprinting, such as the Prader-Willi syndrome (Pfeifer, *Lancet* 356:1819-1820 (2000)). This strategy may also have diagnostic potential for disorders such as preeclampsia, wherein imprinted genes have been hypothesized to play a role (Graves, *Reprod Fertil Dev* 10:23-29 (1998)).

The possible application of fetal DNA in maternal plasma for the prenatal detection of fetal chromosomal aneuploidies is an issue that has been keenly discussed since the discovery of the phenomenon (Lo et al., *Lancet* 350:485-487 (1997); Bianchi, *Am J Hum Genet* 62:763-764 (1998)). The finding of quantitative differences between the circulating fetal DNA levels in aneuploid, compared with euploid pregnancies (Lo et al., *Clin Chem* 45:1747-1751 (1999); Zhong et al., *Prenat Diagn* 20:795-798 (2000)) offers a method for estimating the risk of fetal chromosomal aneuploidies from maternal plasma. The recent discovery of apoptotic fetal cells in maternal plasma ("plasma-derived cells") (Van Wijk et al., *Clin Chem* 46:729-731 (2000)) offers yet another approach for aneuploidy detection from maternal plasma (Poon et al., *Lancet* 356:1819-1820 (2000)). Interestingly, the present data open up yet another potential approach for the detection of fetal chromosomal aneuploidies. This is based on the observation that aberrant DNA methylation patterns may be associated with chromosomal aneuploidy (Kuromitsu et al., *Mol Cell Biol* 17:707-712 (1997); Yu et al., *Proc Natl Acad Sci USA* 94:6862-6867 (1997)). Hence it is possible to develop epigenetic markers for detecting such aberrantly methylated fetal DNA sequences from maternal plasma. Such markers provide specificity compared with a simple quantitation of fetal DNA in maternal plasma (Lo et al., *Clin Chem* 45:1747-1751 (1999); Zhong et al., *Prenat Diagn* 20:795-798 (2000)) and better suitability to large scale application compared with methods based on "plasma-derived cells" (Poon et al., *Lancet* 356:1819-1820 (2000)).

Fetal epigenetic markers may also be used in the analysis of fetal cells isolated from the cellular fraction of maternal blood. This takes advantage of recent data showing that methylation analysis could be performed in an in situ manner (Nuovo et al., *Proc Natl Acad Sci USA* 96:12754-12759 (1999)).

With the recent realization that fetomaternal trafficking is a bidirectional process (Lo et al., *Blood* 88:4390-4395 (1996); Maloney et al., *J Clin Invest* 104:41-47 (1999)), epigenetic markers may also be used to investigate cellular and DNA transfer from the mother to the fetus. Such an approach might also have applications to the investigation of other types of chimerism, such as post-transplantation hemopoietic chimerism (Starzl et al., *Curr Opin Nephrol Hypertens* 6:292-298 (1997)) and urinary DNA chimerism (Zhang et al., *Clin Chem* 45:1741-1746 (1999)).

With our increased understanding of the human genome and the development of high throughput array-based technologies for methylation analysis (Yan et al., *Clin Cancer Res* 6:1432-1438 (2000)), we expect that the number of usable fetal epigenetic markers will rapidly increase over the next few years. Such a development will provide a clinically relevant panel of fetal epigenetic markers which can be used in a synergistic manner with conventional genetic markers in maternal plasma.

What is claimed is:

1. A system for detecting a methylation difference between DNA species originating from cells of a pregnant female and an unborn fetus comprising:
   (i) a cell free biological sample comprising DNA species originating from cells of a pregnant female and an unborn fetus; and
   (ii) a reagent for detecting a methylation difference between the DNA species, wherein the reagent modifies the DNA species differentially depending on the DNA methylation status of the DNA species.

2. The system according to claim 1, wherein the methylation difference is associated with a fetal or maternal disorder.

3. The system according to claim 2, wherein the fetal or maternal disorder is preeclampsia, a chromosomal aneuploidy, trisomy 21 (Down syndrome), Prader Willi Syndrome or Angelman Syndrome.

4. The system according to claim 1, wherein the biological sample is obtained from a second trimester pregnancy.

5. The system according to claim 1, wherein the biological sample is obtained from a third trimester pregnancy.

6. The system according to claim 1, wherein the biological sample is obtained from a pregnant female heterozygous for a biallelic polymorphism.

7. The system according to claim 1, wherein the biological sample is plasma or serum.

8. The system according to claim 1, wherein the DNA species of the fetus comprises an allele that the fetus has inherited from the pregnant female.

9. The system according to claim 1, wherein the DNA species of the fetus comprises a paternally-inherited allele.

10. The system according to claim 1, wherein the reagent comprises sodium bisulfite.

11. The system according to claim 1, further comprising: (iii) a reagent for extracting the DNA species from the biological sample.

12. The system according to claim 1, further comprising: (iii) a nucleic acid mimicking one of the DNA species.

13. The system according to claim 1, further comprising: (iii) PCR primers for amplifying the DNA species to produce an amplicon.

14. The system according to claim 13, wherein the PCR primers are for performing a methylation-specific polymerase chain reaction.

15. The system according to claim 13, wherein the PCR primers are for distinguishing a sequence difference between methylated and unmethylated DNA following bisulfite conversion of the DNA species.

16. The system according to claim 13, wherein at least one of the PCR primers is designed for a methylated DNA sequence.

17. The system according to claim 13, wherein at least one of the PCR primers is designed for an unmethylated DNA sequence.

18. The system according to claim 13, wherein the amplicon is specific for the unborn fetus.

19. The system according to claim 13, further comprising: (iv) a reagent for purifying the amplicon.

20. The system according to claim 11, further comprising: iv) a reagent for sequencing the amplicon.

21. The system according to claim 13, further comprising: (iv) a reagent for detecting the amplicon.

22. The system according to claim 21, wherein the reagent for detecting the amplicon is a gel.

23. The system according to claim 13, further comprising: (iv) a reagent for performing primer extension.

24. The system according to claim 13, further comprising: (iv) a reagent for performing real-time PCR.

25. The system according to claim 13, further comprising: (iv) a marker.

26. The system according to claim 13, further comprising: (iv) EDTA.

27. A system for differentiating human DNA species comprising:
(i) a cell free biological sample comprising human DNA species originating from cells of a pregnant female and an unborn fetus;
(ii) PCR primers for amplifying the human DNA species; and
(iii) a reagent for detecting a methylation difference between the human DNA species, wherein the reagent modifies the DNA species differentially depending on the DNA methylation status of the DNA species.

28. The system according to claim 27, wherein the reagent comprises sodium bisulfite.

29. The system according to claim 27, wherein the biological sample is plasma or serum.

30. A system for amplification of a fetal DNA species comprising:
(i) a cell free biological sample comprising DNA species originating from cells of a pregnant female and an unborn fetus;
(ii) a reagent for isolating the DNA species from the biological sample;
(iii) a reagent for amplifying the fetal DNA species; and
(iv) a regent for detecting a methylation difference between the DNA species originating from cells of the pregnant female and the unborn fetus,
wherein the reagent in (iv) modifies the DNA species differentially depending on the methylation status of the DNA species.

31. The system according to claim 30, wherein the reagent comprises sodium bisulfite.

32. The system according to claim 30, wherein the biological sample is plasma or serum.

* * * * *